US005667783A

United States Patent [19]
Papadakis

[11] Patent Number: 5,667,783
[45] Date of Patent: Sep. 16, 1997

[54] METHOD OF TREATING HIV POSITIVE SUBJECTS

[75] Inventor: Stavros Papadakis, Chicago, Ill.

[73] Assignees: Constantine Alen; Polexene Alen, both of Chicago, Ill.

[21] Appl. No.: 165,270

[22] Filed: Dec. 13, 1993

[51] Int. Cl.$^6$ ............................................. A61K 35/78
[52] U.S. Cl. ...................... 424/195.1; 514/783; 514/934
[58] Field of Search ................... 424/195.1; 514/934, 514/169, 783

[56] References Cited

U.S. PATENT DOCUMENTS

| | | | |
|---|---|---|---|
| 40,189 | 10/1863 | Scott | 424/195.1 |
| 43,118 | 6/1864 | Knoebel | 424/195.1 |
| 65,302 | 5/1867 | Thurmon | 424/195.1 |
| 117,338 | 7/1871 | Simmons | 424/195.1 |
| 132,233 | 10/1872 | Barnes | 424/195.1 |
| 135,083 | 2/1873 | Geomen | 424/195.1 |
| 4,518,591 | 5/1985 | Iida | 424/195.1 |
| 4,716,120 | 12/1987 | Tsay | 436/513 |
| 5,002,938 | 3/1991 | Wang et al. | 514/171 |

OTHER PUBLICATIONS

Nene et al., *Labder. J. Sci. Tech B*, vol. 6, pp. 226–228, (1968)→Abstract Only see search report.
Saxena et al., *Curr. Sci*, vol. 44(19), p. 723, (1975)→Abstract Only see search report.
Abdel–Gawad et al., *Fitoterapia*, vol. 47, p. 111, (1976)→Abstract Only see search report.
Fell et al. *J. Pharm. Pharmacol.*, vol. 20, pp. 646–649, (1968)→Abstract only see search report.
Greene, *Scientific American*, pp. 90–105, (Sep. 93).
Fauci, *Science*, vol. 262, pp. 1011–1018, (12 Nov. 93).
Bonsignore et al., *Fitoterapia*, vol. 61/4, pp. 339–341, (1990)→Abstract Only see search report.
Dafni et al., *J. Ethnopharmacol.*, vol. 10, pp. 295–310, (1984)→Abstract Only see search report.
Singh et al., *Indian J. Chem*, vol. 12 (12), pp. 1325–1237, (1974)→Abstract Only see search report.
Hamanouda et al., Chem. and Pharm. Studies A. Microcarpas, PLMEAA 22(2):109–212, 1972.
King J. American Dispensatory 8th Ed Cincinnati 1870 pp. 965–967.
Steinmentz E. F. Codey Vegetabilis 1951 Amsterdam #161.
Bailey, Standard Cyclopedia of Horticulture, Macmillan Co., New York, 1935.
Chittenden, Dictionary of Gardening, Clarendon Press, Oxford.
Fell et al. *J. Pharm. Pharmac.* 20:646–649 (1968).
Hommouda et al., Chemical and Pharmacological Studies of *Asphodelus Microcarpus*, PLMEAA 22(2) 109–212 (1972).
Hammouda et al., Die Pharmazie, Pharmazie 29, H. 9 (1974).
Madaan et al., Indian Journal of Biochemistry & Biophysics vol. 10, Mar. 1973, pp. 55–58.
Scarborough, Clinics in Plastic Surgery, vol. 10/Nov. 4, Oct., 1983.
R.M.T. Dahlgren, et al., The Families of Monocotyledons––Struc Evolution and Taxonomy, Springer–Verlag, New York, (1985).
Aids and the Election, Scientific American, vol. 259, No. 4, p. 14 (1988).
AIDS: an Unknown Distance Still to Go, Scientific American, vol. 259, No. 4, p. 152 (1988).
AIDS IN, Scientific American, vol. 259, No. 4, p. 40 (1988).
The Molecular Biology of the AIDS VIRUS, Scientific American, Vol. 259, No. 4, pp. 52 (1988).
The Origins of the AIDS Virus, Scientific American, vol. 259, No. 4, p. 90 (1988).
HIV Infection: the Clinical Picture, Scientific American, vol. 259, No. 4, p. 90 (1988).
HIV Infection: the Cellular Picture, Scientific American, vol. 259, No. 4, p. 100 (1988).
AIDS Therapies, Scientific American,, vol. 259, No. 4, p. 110 (1988).
AIDS Vaccines, Scientific American, vol. 259, No. 4, p. 120 (1988).
The Epidemiology of AIDS in the U.S., Scientific American, vol. 259, No. 4, p. 72 (1988).
The Social Dimension of AIDS, Scientific American, vol. 259, No. 4, p. 128 (1988).
The International Epidemiology of AIDS, Scientific American, vol. 259, No. 4, p. 82 (1988).

*Primary Examiner*—John Kight
*Assistant Examiner*—Howard C. Lee
*Attorney, Agent, or Firm*—Laff, Whitesel, Conte & Saret, Ltd.

[57] ABSTRACT

A method of lowering p24 (HIV) antigen to not more than 40 picograms/ml in an HIV positive subject by the administration of a therapeutically active composition is disclosed. The composition includes as an active pharmaceutical an extract of at least one plant of the Asphodelus genus and the *tenuifolius* species or the chemical equivalent thereof. The plant extract includes an aqueous extract of a woody stem, a root system, a plurality of loculicidal capsules, and a plurality of seeds. The plant extract is admixed with a pharmaceutically acceptable carrier such as water.

14 Claims, No Drawings

METHOD OF TREATING HIV POSITIVE SUBJECTS

The subject matter, in its entirety, of U.S. Pat. No. 5,091,181 (issued Feb. 25, 1992) is incorporated by reference herein.

FIELD OF THE INVENTION

This invention relates to a method for treating HIV positive subjects. More particularly, this invention relates to a method for treating HIV positive subjects wherein the composition combats the virus.

BACKGROUND OF THE INVENTION

To date, there are several widespread diseases that are often fatal and which generally involve a certain type of white blood cell that is responsible for orchestrating the immune system of the body. Among such diseases are adult T-Cell leukemia (ATL) and acquired immunodeficiency syndrome (AIDS). These diseases not only infect the same type of white blood cell, but further share another crucial feature in that they are all caused by a class of infectious agents known as retroviruses.

Retroviruses are viruses that cannot replicate without controlling and exploiting the biosynthetic apparatus of a cell for different purposes. Retroviruses consist of the genetic material of RNA and are capable of reversing the ordinary flow of genetic information (from DNA to RNA to proteins). Additionally, retroviruses carry an enzyme called reverse transcriptase which uses the viral RNA as a template for making DNA. The viral DNA integrates itself into the genome of the host wherein it remains latent until it is activated to make new virus particles. Much attention is being paid to the human immunodeficiency virus (HIV) retrovirus which causes AIDS due to its rapid transmission, progressive derangement of immune function, and high fatality rate.

It appears that the HIV retrovirus enters a cell by binding to a molecule known as the CD4 antigen. The CD4 antigen is found primarily on a specific set of white blood cells of the immune system called T4 lymphocytes or helper T-cells. Accordingly, HIV infection is characterized by the loss of these T-lymphocyte cells which causes a deterioration of the immune system.

The T-lymphocyte cell is crucial to the immune system in that, among other functions, it recognizes foreign antigens, markers, or infected cells, and helps to activate another set of lymphocyte white blood cells which multiply and produce antibodies that bind to infected cells. The T-lymphocyte cell further is capable of completely eliminating infected cells. Thus, the loss of T-lymphocyte cells not only seriously impairs the body's ability to fight most invaders, but also has a severe impact on the defenses against viruses, fungi, parasites, and certain bacteria.

In the case of AIDS and some forms of hepatitis and leukemia, it is the secondary infections which are the actual cause of death. My previous patent, U.S. Pat. No. 5,091,181 was directed to the need for treating such immune deficiency-causing diseases by means that would boost the suppressed lymphocyte levels and provide a defense against life-threatening secondary infections.

Presently, there is no known cure for AIDS. There are, however, various experimental drugs on the market, including an antiviral substance known as azidothymidine (AZT) which has been shown to prolong the lives of certain AIDS subjects. These drugs are, for the most part, extremely expensive and often difficult to obtain.

Thus, although there is no cure for AIDS, early intervention with antiretroviral therapy can substantially decrease the risk of opportunistic infections and may improve the survival of subjects with HIV infection. Accordingly, a procedure to detect the virus itself rather than the immune response to the virus is critical.

There are several known diagnostic techniques for detecting HIV infection in adults and children. One such diagnostic technique is the immune-complex-dissociated HIV p24 antigen assay which is a rapid, simple serologic test that may be used to diagnose HIV infection. The p24 antigen of human immunodeficiency virus type 1 (HIV-1) is sometimes detected before antibody (anti-HIV-1) is detectable in the serum of recently infected persons. This is because the p24 antigen is usually present in the circulation of the HIV-infected subject shortly after infection with HIV-1 and before the development of a humoral response. Thus, the HIV p24 antigen assay reveals the presence of circulating p24 antigen which appears to stimulate the often rapid development of the AIDS virus.

Accordingly, it is an object of the present invention to provide a method for treating HIV positive subjects to combat the virus.

A further object of the present invention is to provide a method for treating HIV positive subjects that is easily administered to the subject and which is relatively inexpensive.

Yet another object of the present invention is to provide a method for treating HIV positive subjects.

The objectives and advantages of the present invention are achieved by providing a method for treating HIV positive subjects by administering an effective amount of a therapeutically active composition to a subject. The composition used in the method has a medicinal application and has resulted in a negative reading for the p24 (HIV) antigen in a subject that initially tested positive for the p24 (HIV) antigen. Also, the composition used in the method maintained a negative reading for the p24 (HIV) antigen in a subject that initially tested negative for the p24 (HIV) antigen.

The foregoing composition used in the inventive method includes as an active pharmaceutical an extract of at least one edible plant or herb. Specifically, the herb is a Mediterranean and West Asiatic plant known as *Asphodelus tenuifolius*. The genus Asphodelus describes a hardy, herbaceous stemless plant having white, lily-like flowers in long racemes, fleshy fascicled roots and firm, linear, radical, tufted leaves. It generally grows as a common weed in the above-cited locations.

More specifically, the composition derives from one species of asphodel, a purple-flowering variant of *Asphodelus tenuifolius* which occurs in Greece and Turkey. This identification is based on R. M. T. Dahlgren, et al's "The Families of Monocotyledons—Structure, Evolution and Taxonomy", Springer-Verlag, New York (1985).

Minor discrepancies of plant classification are often found between different botanists' works. Therefore, *A. tenuifolius* has been described as "identical" to *A. microcarpus* and *A. aestivus* by some classifiers of the plant (see Bailey, Standard Cyclopedia of Horticulture, Macmillan Co., New York, 1935), and alternatively as "allied to" *A. Fistulosis* by others (see Chittenden, Dictionary of Gardening, Clarendon Press Oxford, 1956). These species are closely related. Accordingly, it is expected that asphodel species other than

*A. tenuifolius* will be identified which will yield an equally therapeutic composition.

My U.S. Pat. No. 5,091,181 is directed to providing a composition for increasing the white cell levels in subjects by use of an herbal composition. The composition used in that patent is the same as is used in this invention. However, I have also provided the additional composition of using a mixture of the herbal extract of U.S. Pat. No. 5,091,181 with a cortisone.

Thus, the inventive method herein involves treating HIV positive subjects with an extract derived from an edible plant known as *Asphodelus tenuifolius* or its chemical equivalent. The plant is collected in its dry form. A certain methodology has been developed for the extraction process (see U.S. Pat. No. 5,091,181). This methodology involves using the entire plant in the production of the extract, including the whole woody stem, the root system, the loculicidal capsules, and the seeds. The extract dosage for each subject is approximately 150 mls per dose. The extract is administered orally, twice a day with a 10–12 hour interval in between the doses. The average treatment for high risk cases lasts 30–45 days (i.e., full blown AIDS), and for simple cases the treatment lasts for 10–20 days (i.e., HIV positive). All subjects who underwent treatment were under the supervision of their private doctors. Moreover, it was recommended that the subjects undergo daily non-strenuous, light exercises along with a specific low fat diet program.

Prior to the Examples as hereinafter set forth wherein various subjects ingested the extract, the toxicity of the plant extract used in the inventive method was tested in two independent toxicity studies. Each study was directed to examining the behavioral and physiological aspects of laboratory animals which were given the plant extract.

The first study involved using five rabbits as models. Animal rooms and cages were cleansed and sanitized prior to initiating the study and then weekly thereafter. The light/dark cycle in the animal rooms and cages was kept on a 12L:12D schedule while the temperature was maintained at 70–75 degrees Fahrenheit. The normal water supply of the test animals was replaced with the plant extract for a two week period. Thereafter, city quality tap water was again supplied. No irregularities in the animals' behavior subsequent to plant extract consumption were noted. Thus, the non-toxicity of the extract was confirmed. Moreover, two days after returning the animals back to the tap water, a limited gross necropsy was performed on two of the animals to examine any change in the internal organs. No apparent changes were observed in these animals. The rest of the animals were examined again after a two month period and there were still no discernible effects on the animals. The first study lasted approximately two months.

A second toxicity study was carried out with a group of ten mice. This study involved varying the concentration of the extract. The variable concentrations were calculated by ratios between parts of the plant weight in grams and solvent volume. Thus, the mice were administered 1 ml doses of plant extract at concentrations of 25%, 50%, and 100%. Again, no adverse reactions were noted. The test animals appeared normal irrespective of dose, supporting a second conclusion of non-toxicity. All animals were kept in accordance with accepted animal care practice.

DETAILED DESCRIPTION OF THE INVENTION

The present invention contemplates a method for treating HIV positive subjects by administering an effective amount of a therapeutically active composition to a subject. The compositions used resulted in a negative reading for the p24 (HIV) antigen in a group of subjects who initially tested positive for the p24 (HIV) antigen. Also, the composition used in the method maintains a negative reading for the p24 (HIV) antigen in a subject that initially tested negative for the p24 (HIV) antigen.

Therefore, it is concluded that the composition either neutralizes, destroys or, in some manner, inhibits the HIV virus.

My composition is prepared by collecting and washing approximately three or four dry *Asphodelus tenuifolius* plants. The entire plant is included in the extract, including the whole woody stem, the root system, the loculicidal capsules, and the seeds. Each loculicidal capsule contains from five to six seeds, with the number of seeds on one plant being within the range of 300–500 depending on the plant's growth. About 40 to about 60 grams (which corresponds to three or four plants of *Asphodelus tenuifolius* are placed into about 1.5 to 2.5 liters, and preferably about 2 liters of water. The water is then boiled for about twenty minutes during which time the extraction process occurs. Approximately 600 milliliters of the water evaporates during boiling. A residue will form during the extraction process. The residue along with the boiled plant(s) are removed by filtering so that the remaining solution contains only the *Asphodelus tenuifolius* extract mixed in with the water. The plant extract solution is preferably stored in a dark, cool environment having a temperature of from about 4° C. to about 8° C. About 150 to about 170 mls per dose is ingested by each subject. The plant extract is administered orally, twice a day with a 10–12 hour interval in between the doses. In a preferred embodiment about 50 to about 500 mg of a cortisone product is dissolved in about 150 to about 170 ml dose and this is administered to the subjects for at least 5 days. The average treatment lasts for 10–45 days. This varies depending on the subject. All subjects undergoing treatment were under the supervision of their private doctors. Moreover, it was recommended that the subjects undergo daily non-strenuous, light exercises along with a specific low fat diet program.

Nine HIV positive male human subjects were treated by the inventive method. They were between the ages of 30 to 66 years old and were each in the high risk group. However, most of the subjects were asymptomatic. All nine subjects were examined for blood cell counts prior to the plant extract treatment. The subclasses of T-cells (T3, T4, T8) were studied before treatment, sometimes after approximately ten days, and at the end of each treatment. The plant extract was supplied to each subject twice daily in oral dosages of 150–170 ml each.

For each subject, one of the doses on each the first and second day there was dissolved about 125mg (a ¼ of 500 mg tablet) of the cortisone Medrol which is described as 1-dehydro-6-α-methylhydrocortisone by the 10th Edition of Merck Index p. 875 (5984). On each of the 3rd and 4th days there was dissolved 250 mg (½ tablet) of Medrol in one of the doses. On the fifth day there was dissolved 500 mg (1 tablet) in one of the doses. One each of the sixth and seventh days I dissolved 250 mg in one of the doses. Finally on each of the eighth and ninth days I dissolved 125 mg in one of the doses.

Each of the nine subjects was subjected to the following tests:

(a) p24 antigen test (if more than 40 picograms of the p24 antigen was detected in a subject, then that subject was considered as testing positive);

(b) T-Cell count;

(c) hematological tests (identification of white blood cell types, and blood cell types);

(d) biochemical test;

(e) blood electrolyte variations; and (f) protein electrophoresis.

The following clinical data (below) was compiled for each of the nine HIV positive subjects treated by the inventive method. The units for measurement, as well as the standard values, are the same for all tests performed for each of the nine subjects.

SUBJECT NO. 1

Subject No. 1 belongs to the high risk HIV positive group. Subject No. 1 was taking AZT and INTERFERON prior to the extract treatment. Subject No. 1 was treated from Oct. 16, 1992 to Nov. 9, 1992. Blood for the Oct. 16, 1992 tests was taken prior to treatment and blood for the Nov. 9, 1992 test was taken after treatment.

Subject No. 1 was tested for the p24 antigen (HIV-AG). Table No. 1 (below) shows the results of the HIV-AG and T-Cell tests. As shown in the table, Subject No. 1 had a positive HIV-AG before treatment with the plant extract and a negative HIV-AG after less than one month of treatment.

TABLE 1

| HIV-AG T CELLS | OCT 16 1992 POSITIVE | OCT 27 1992 | NOV 9 1992 NEGATIVE |
|---|---|---|---|
| ANL % | 32 | 34 | 35 |
| ANL | 1472 | 1258 | 1365 |
| T3% | 77 | 75 | 81 |
| T3 | 1133 | 943 | 1105 |
| T4% | 7 | 4 | 12 |
| T4 | 103 | 50 | 163 |
| T8% | 70 | 70 | 66 |
| T8 | 1030 | 880 | 900 |

Table 2 (below) represents specific changes in the white blood cell types of Subject No. 1 before treatment. The first three columns represent test results prior to treatment with the plant extract. The next four columns represent the changes in the number of white blood cells of the subject during the treatment. As shown in table 2, the lymphocytes increased in number most dramatically during days 10–20 of treatment. Likewise, the neutrophils experienced the largest increase during that same time period. The monocytes were remarkably constant with the exception of a decrease on approximately day 17 of treatment.

TABLE 2

| | Oct 14 1992 | Oct 15 1992 | Oct 16 1992 | Oct 21 1992 | Oct 27 1992 | Nov 2 1992 | Nov 9 1992 |
|---|---|---|---|---|---|---|---|
| WBC TYPES | | | | | | | |
| Lymphocytes | 28 | 30 | 32 | 30 | 34 | 35 | 26 |
| Monocytes | 23 | 20 | 19 | 24 | 18 | 8 | 21 |
| Eisinophils | — | — | — | — | — | — | — |
| Basophils | — | — | — | — | — | — | — |
| Neutrophils | 49 | 50 | 49 | 46 | 48 | 57 | 53 |

Table 3 (below) shows various blood test results taken before, during, and at the end of the treatment with the plant extract. The first three columns represent tests taken before treatment. Columns 4 to 7 represent tests taken after treatment. As the data in table 3 indicates, there is a general increase in each of the different types of blood cells, with the exception of the white blood cells, the MCH, the LYM, and the NEUT cells which remained more or less constant.

TABLE 3

| | Oct 14 1992 | Oct 15 1992 | Oct 16 1992 | Oct 21 1992 | Oct 27 1992 | Nov 2 1992 | Nov 9 1992 |
|---|---|---|---|---|---|---|---|
| Blood Cells | | | | | | | |
| WBC | 5.1 | 4.3 | 4.6 | 3.6 | 3.7 | 3.9 | 3.0 |
| RBC | 3.13 | 3.02 | 3.09 | 3.16 | 3.31 | 3.34 | 3.4 |
| HNb | 11.6 | 11.3 | 11.5 | 11.7 | 12.1 | 12.8 | 12.4 |
| HCT | 35.6 | 34.4 | 35.3 | 36.0 | 37.7 | 38.2 | 38.1 |
| MCV | 113.7 | 113.9 | 114.2 | 113.9 | 113.9 | 114.4 | 112.1 |
| MCH | 37.1 | 37.4 | 37.2 | 37.0 | 36.6 | 38.3 | 36.5 |
| MCHC | 32.6 | 32.8 | 32.6 | 32.5 | 32.1 | 33.5 | 32.5 |
| PLT | 246 | 237 | 234 | 237 | 293 | 287 | 222 |
| LYM % | 28.4 | 30.0 | 32.2 | 30.5 | 33.9 | 32.2 | 26.4 |
| MID % | 22.7 | 19.6 | 19.0 | 23.9 | 17.9 | — | 21.5 |
| NEUT % | 48.9 | 50.4 | 48.8 | 45.6 | 48.2 | — | 52.1 |
| LYM | 1.4 | 1.3 | 1.5 | 1.1 | 1.3 | 1.3 | 0.8 |
| MID | 1.2 | 0.8 | 0.9 | 0.9 | 0.7 | — | 0.6 |
| NEUT | 2.5 | 2.2 | 2.2 | 1.6 | 1.7 | — | 1.6 |
| RDW-CV | 11.4 | 11.5 | 11.3 | 11.8 | 12.0 | 12.6 | 12.6 |
| PDW | 12.5 | 12.5 | 11.6 | 12.1 | 12.3 | 11.8 | 12.2 |
| MPV | 9.9 | 9.8 | 9.7 | 9.6 | 9.9 | 9.8 | 10.1 |
| P-LCR | 25.5 | 24.1 | 23.1 | 22.9 | 25.7 | 24.7 | 27.0 |

Table 4 (below) discloses the biochemical status of Subject No. 1. The first column represents the status of the subject prior to treatment with the plant extract. Columns 2 and 3 show results of biochemical tests during and at the end of treatment, respectively. Likewise, columns four and five show the measurements units and the normal values, respectively, of the different biochemical tests. As shown in table 4, many of the biochemical tests (i.e., cholesterol, HDL, LDL, phosphorus) showed increases during treatment of Subject No. 1 whereas, most of the biochemical tests (urea, cholesterol, HDL, LDL, triglycerides) showed an overall increase only by the end of the treatment. In contrast, the data for creatinine remained the same by the end of the treatment, while data for phosphorus and magnesium showed a slight decrease. There was no data for the calcium level of Subject No. 1 prior to treatment. However, the calcium level data showed a decrease by the end of the treatment. All of the data was within the range of normal values (shown in the fifth column), with the exception of the HDL, LDL, and triglycerides data.

TABLE 4

| Biochemical Tests | Oct 16 1992 | Oct 27 1992 | Nov 9 1992 | Units | Normal Values |
|---|---|---|---|---|---|
| Urea | 30 | 30 | 36 | mg/100 ml | 15–55 |
| Cholesterol | 158 | 181 | 180 | " | 125–260 |
| HDL | 29 | 33 | 31 | " | 30–65 |
| LDL | 96 | 114 | 107 | " | 88–188 |
| Triglycerides | 189 | 170 | 212 | " | 40–160 |
| Creatinine | 1.2 | 1.1 | 1.2 | " | 0.9–1.5 |
| Calcium | — | 9.5 | 9.0 | " | 8.1–10.4 |
| Phosphorus | 3.1 | 3.3 | 3.0 | " | 2.5–4.5 |
| Magnesium | 2.0 | 2.0 | 1.9 | mEq/l | 1.7–2.4 |

Table 5 (below) shows changes in blood electrolytes of Subject No. 1. All values are measured in mEq/l. The first column shows the results before treatment with the plant extract. The second and third columns reflect data accumulated during and the end of treatment, respectively. The fourth column shows normal values for blood electrolyte data. As indicated in the table, all of the values were within the normal ranges. There were increases in the potassium, sodium, chloride, gamma-GT, and Alp electrolytes from prior to treatment to the end of treatment. The trans-Go electrolytes decreased while the trans-GP remained the same.

TABLE 5

| Electrolytes | OCT 16 1992 | OCT 27 1992 | NOV 9 1992 | Normal Values |
|---|---|---|---|---|
| K | 4.5 | 5.7 | 4.8 | 3.5–5.1 |
| Na | 138 | 133 | 141 | 136–146 |
| Cl | 106 | 102 | 102 | 98–107 |
| Trans-Go | 30 | 20 | 25 | 5–40 |
| Trans-GP | 20 | 15 | 20 | 5–40 |
| γ-GT | 24 | 30 | 35 | 10–50 |
| Alp | 66 | 83 | 67 | 30–125 |

Table 6 (below) shows the results of electrophoresis for Subject No. 1. The first column shows the results before treatment with the plant extract, the second column shows the results during treatment, and the third column shows the results at the end of the treatment. The fourth column shows the normal values. As shown in table 5, most of the protein electrophoresis data (i.e., albumin, a1, gamma) is within the range of normal values by the end of the treatment. The only increases among the data were in the albumin and albumin to globulin ratio.

TABLE 6

| Protein Electrophoresis | OCT 16 1992 | OCT 27 1992 | NOV 9 1992 | Normal Values |
|---|---|---|---|---|
| ALBUMIN | 50.3 | 54.9 | 55.5 | 52–65 |
| a1 | 3.3 | 3.5 | 3.3 | 2–4.5 |
| a2 | 9.1 | 9.4 | 8.7 | 11–15 |
| β | 16.7 | 15.3 | 14.1 | 6–13 |
| γ | 20.6 | 16.9 | 18.4 | 10–19 |
| Alb/Glob[1] | 1.01 | 1.22 | 1.25 | |

[1].Ratio between Albumin to Globulin

SUBJECT NO. 2

This HIV positive and asymptomatic subject was taking AZT primarily and later DDL. Subject No. 2 was treated in the same manner as Subject No. 1. Specifically, subject No. 2 was treated from Oct. 16, 1992 to Nov. 11, 1992. Blood for the Oct. 16, 1992 test was taken prior to treatment, while blood for the Nov. 11, 1992 test was taken after treatment. The units for measurement as well as the standard values are the same as with Subject No. 1.

Table 7 (below) shows the results of the HIV-AG and T-cell tests. Subject No. 2 was HIV-AG positive before treatment and HIV-AG negative after less than one month of treatment. As the table indicates, the T-cells generally decreased or remained the same over the time period beginning prior to treatment until after the treatment.

TABLE 7

| HIV-AG T CELLS | OCT 16 1992 POSITIVE | OCT 20 1992 | NOV 11 1992 NEGATIVE |
|---|---|---|---|
| ANL % | 35 | 39 | 28 |
| ANL | 840 | 858 | 532 |
| T3% | 77 | 62 | 63 |
| T3 | 1192 | 330 | 335 |
| T4% | 5 | 3 | 5 |
| T4 | 42 | 16 | 26 |
| T8% | 69 | 50 | 55 |
| T8 | 579 | 266 | 292 |

Table 8 (below) represents specific changes in white blood cell types of Subject No. 2. The first three columns show the test results prior to treatment with the plant extract. The next four columns represent the changes in white blood cells types during the treatment. As the data in the table reveals, the lymphocytes decreased while the monocytes and neutrophils increased.

TABLE 8

| | Oct 14 1992 | Oct 15 1992 | Oct 16 1992 | Oct 21 1992 | Oct 29 1992 | Nov 5 1992 | Nov 11 1992 |
|---|---|---|---|---|---|---|---|
| WBC TYPES | | | | | | | |
| Lymphocytes | 48 | 40 | 35 | 29 | 39 | 41 | 28 |
| Monocytes | 13 | 11 | 10 | 15 | 14 | 18 | 19 |
| Eosinophils | — | 1 | — | — | — | — | — |
| Basophils | — | — | — | — | — | — | — |
| Neutrophils | 39 | 48 | 65 | 56 | 47 | 41 | 53 |

Table 9 (below) shows various blood test results taken before, during, and at the end of the treatment with the plant extract. The first three columns in the table represent tests taken before treatment. Columns four to seven represent tests taken after treatment. Most of the test data (WBC, MCV, MCH, HC, PLT, LYM%, LYM, PDW, MPV, P-LCR) showed an overall decrease over the course of the treatment. However, the data for the white blood cells and the platelets showed an increase during days 10–20 of the treatment but a decrease at the end of the treatment.

TABLE 9

| | Oct 14 1992 | Oct 15 1992 | Oct 16 1992 | Oct 21 1992 | Oct 29 1992 | Nov 5 1992 | Nov 11 1992 |
|---|---|---|---|---|---|---|---|
| Blood Cells | | | | | | | |
| WBC | 2.4 | 2.4 | 2.4 | 1.6 | 2.2 | 3.0 | 1.9 |
| RBC | 3.47 | 3.43 | 3.55 | 3.23 | 3.83 | 3.69 | 3.71 |
| Hb | 11.8 | 11.7 | 12.1 | 10.9 | 12.3 | 12.0 | 11.9 |
| HT | 36.5 | 36.0 | 37.1 | 33.4 | 38.6 | 36.8 | 36.9 |
| MCV | 105.2 | 105.0 | 104.5 | 103.4 | 100.8 | 99.7 | 99.5 |
| MCH | 34.0 | 34.1 | 34.1 | 33.7 | 32.1 | 32.5 | 32.1 |
| HC | 32.3 | 32.5 | 32.6 | 32.6 | 31.9 | 32.6 | 32.2 |
| PLT | 166 | 161 | 162 | 165 | 220 | 206 | 160 |
| LYM % | 48.2 | 42.3 | 35.3 | 28.9 | 38.7 | 41.4 | 28.4 |
| MID % | 12.9 | — | 10.1 | 14.9 | 13.8 | 18.0 | 26.2 |
| NEUT % | 38.9 | — | 54.6 | 56.2 | 47.5 | 40.6 | 45.4 |
| LYM | 1.2 | 1.0 | 0.8 | 0.5 | 0.9 | 1.2 | 0.5 |
| MID | 0.3 | — | 0.2 | 0.2 | 0.3 | 0.5 | 0.5 |
| NEUT | 0.9 | — | 1.4 | 0.9 | 1.0 | 1.3 | 0.9 |
| RDW- | 12.1 | 12.2 | 11.4 | 12.1 | 12.1 | 12.9 | 12.8 |

TABLE 9-continued

|  | Oct 14 1992 | Oct 15 1992 | Oct 16 1992 | Oct 21 1992 | Oct 29 1992 | Nov 5 1992 | Nov 11 1992 |
|---|---|---|---|---|---|---|---|
| CV |  |  |  |  |  |  |  |
| PDW | 15.4 | 14.7 | 14.8 | 12.6 | 14.7 | 13.6 | 13.6 |
| MPV | 11.3 | 11.5 | 11.4 | 11.0 | 11.4 | 10.9 | 11.0 |
| P-LCR | 37.0 | 37.9 | 36.8 | 33.1 | 36.5 | 32.3 | 32.2 |

Table 10 (below) represents the biochemical status of Subject No. 2. The first column represents the status of the subject prior to treatment with the plant extract. Columns 2 and 3 show data for biochemical tests performed during treatment and at the end of treatment. The fourth and fifth columns reflect the measurement units and the normal values for each of the biochemical tests. As the table indicates, there was an overall increase in the cholesterol, triglycerides, and calcium of Subject No. 2 during the course of treatment. With the exception of the biochemical test for HDL, all of the tests showed data that was within the range of normal values by the end of the treatment.

TABLE 10

| Biochemical tests | Oct 16 1992 | Oct 29 1992 | Nov 11 1992 | Units | Normal Values |
|---|---|---|---|---|---|
| Urea | 29 | 36 | 27 | mg/100 ml | 15–55 |
| Cholesterol | 171 | 142 | 172 | " | 125–260 |
| HDL | 29 | 23 | 29 | " | 30–65 |
| LDL | 130 | 91 | 130 | " | 88–188 |
| Triglycerides | 61 | 105 | 68 | " | 40–160 |
| Creatinine | 1.2 | 1.1 | 1.0 | " | 0.9–1.5 |
| Calcium | 3.1 | 9.1 | 8.9 | " | 8.1–10.4 |
| Phosphorus | 3.2 | 3.9 | 3.2 | " | 2.5–4.5 |
| Magnesium | 2.0 | 2.1 | 2.0 | mEq/l | 1.7–2.4 |

Table 11 (below) shows changes in the blood electrolytes of Subject No. 2. All values were measured in mEq/. The first column represents the results before treatment with the plant extract. The second and third columns represent during treatment and the end of treatment, respectively. The fourth column reflects the range of normal values for each of the above tests. As shown in table 11, the various blood electrolytes increased over the course of the treatment, except for the potassium and chloride electrolytes. All of the tests show data within the range of normal values for each of the tests by the end of the treatment.

TABLE 11

| Electrolytes | Oct 16 1992 | Oct 29 1992 | Nov 11 1992 | Normal Values |
|---|---|---|---|---|
| K | 4.4 | 4.2 | 4.2 | 3.5–5.1 |
| Na | 135 | 137 | 144 | 136–146 |
| Cl | 107 | 102 | 98 | 98–107 |
| Trans-Go | 28 | 30 | 30 | 5–40 |
| Trans-GP | 18 | 21 | 38 | 5–40 |
| γ-GT | 15 | 20 | 40 | 10–50 |
| Alp | 48 | 62 | 66 | 30–125 |

Table 12 (below) discloses the results from the protein electrophoresis of Subject No. 2. The first column reflects the data before treatment with the plant extract. The second column shows data during treatment. The third column shows data at the end of treatment. The fourth column indicates the range of normal values. As shown in table 12, increases in data occurred only in Alb and Alb/Glob ratio, with the highest increases being during days 10–20 of the treatment. The data in table 12 also reflects that the protein electrophoresis was within the range of normal values, with the exception of the Alb (which was within the range of normal values only during the middle of the treatment), a2, and gamma.

TABLE 12

| Protein Electrophoresis | Oct 16 1992 | Oct 29 1992 | Nov 11 1992 | Normal Values |
|---|---|---|---|---|
| Alb | 46.4 | 53.1 | 49.4 | 52–65 |
| a1 | 2.9 | 2.2 | 2.8 | 2–4.5 |
| a2 | 7.5 | 6.4 | 7.6 | 11–15 |
| β | 12.9 | 10.1 | 12.7 | 6–13 |
| γ | 30.3 | 28.2 | 27.5 | 10–19 |
| Alb/Glob | 0.87 | 1.13 | 0.98 |  |

SUBJECT NO. 3

Subject No. 3 was suffering from a number of allergies. Subject No. 3 was not on any type of medication other than Ginseng and other herbal serums. Subject No. 3 was treated from Oct. 16, 1992 to Nov. 16, 1992. Blood for the Oct. 16, 1992 test was taken prior to treatment and blood for the Nov. 16, 1992 test was taken after treatment. The same type of testing was performed on Subject No. 3 as with the previous subjects. The units for measurement, as well as the standard values, are the same for Subject No. 3 as with the prior subjects.

Table 13 (below) shows another positive result. Subject No. 3 was initially tested for the p24 antigen (HIV-AG) and revealed a positive HIV-AG before treatment with the plant extract and a negative HIV-AG after less than one month of treatment. As shown in table 13, the T3 and T4 cells increased, while the T8 cells remained the same.

TABLE 13

| HIV-AG T CELLS | OCT 16 1992 POSITIVE | NOV 9 1992 | NOV 16 1992 NEGATIVE |
|---|---|---|---|
| ANL % | 50 | 30 | 29 |
| ANL | 2300 | 2250 | 2581 |
| T3% | 87 | 85 | 81 |
| T3 | 2001 | 1912 | 2090 |
| T4% | 19 | 16 | 18 |
| T4 | 437 | 360 | 464 |
| T8% | 60 | 62 | 60 |
| T8 | 1380 | 1385 | 1548 |

Table 14 (below) represents specific changes in the white blood cell types of Subject No. 3 before treatment with the plant extract. The first three columns show the test results before treatment. The last three columns represent the changes of white blood types during treatment. As shown in table 14, the lymphocytes, monocytes, and eosinophils decreased, while the increased in number.

TABLE 14

| WBC TYPES | Oct 14 1992 | Oct 15 1992 | Oct 16 1992 | Oct 29 1992 | Nov 9 1992 | Nov 16 1992 |
|---|---|---|---|---|---|---|
| Lymphocytes | 44 | 46 | 50 | 50 | 30 | 29 |
| Monocytes | 21 | 14 | 17 | 9 | 7 | 6 |
| Eosinophils | — | 4 | — | — | 3 | 3 |
| Basophils | — | — | — | — | — | — |
| Neutrophils | 35 | 36 | 33 | 41 | 60 | 62 |

Table 15 (below) shows various blood test results taken before, during, and at the end of treatment with the plant extract. The first three columns represent tests taken before treatment. Columns four to six represent tests taken after treatment. As shown in table 15, the data for the white blood cells reflects an increase by almost half. Increases were also shown in the red blood cells, the hemoglobin, HCT, MCV, MCH, PLT, LYM%, NEUT%, LYM, NEUT, and PDW. Most of the increases were reflected in days 10–20 of the treatment. The MID% decreased, whereas the MCHC, MID, RDW-CV, MP, and P-LCR remained approximately the same.

TABLE 15

| | Oct 14 1992 | Oct 15 1992 | Oct 16 1992 | Oct 29 1992 | Nov 9 1992 | Nov 16 1992 |
|---|---|---|---|---|---|---|
| Blood Cells | | | | | | |
| WBC | 4.7 | 4.7 | 4.6 | 7.1 | 7.5 | 8.9 |
| RBC | 4.64 | 4.54 | 4.69 | 5.02 | 4.64 | 4.48 |
| Hb | 13.5 | 13.5 | 13.9 | 15.0 | 13.9 | 13.2 |
| HCT | 41.3 | 40.5 | 42.3 | 45.0 | 42.2 | 40.3 |
| MCV | 89.0 | 89.2 | 90.2 | 89.6 | 90.9 | 90.0 |
| MCH | 29.1 | 29.7 | 29.6 | 29.9 | 30.0 | 29.5 |
| MCHC | 32.7 | 33.3 | 32.9 | 33.3 | 32.9 | 32.8 |
| PLT | 324 | 322 | 299 | 290 | 344 | 439 |
| LYM % | 44.1 | 44.8 | 50.1 | 49.6 | 30.6 | 29.5 |
| MID % | 21.2 | 19.7 | 16.8 | 8.7 | 12.2 | 10.2 |
| NEUT % | 34.7 | 35.5 | 33.1 | 41.7 | 57.2 | 60.3 |
| LYM | 2.1 | 2.1 | 2.3 | 3.5 | 2.3 | 2.6 |
| MID | 1.0 | 0.9 | 0.8 | 0.6 | 0.9 | 0.9 |
| NEUT | 1.6 | 1.7 | 1.5 | 3.0 | 4.3 | 5.4 |
| RDW-CV | 12.9 | 13.5 | 12.6 | 13.1 | 13.1 | 12.7 |
| PDW | 14.7 | 14.0 | 13.0 | 14.1 | 15.0 | 14.9 |
| MP | 11.3 | 10.6 | 10.5 | 10.8 | 11.2 | 11.1 |
| P-LCR | 36.3 | 31.2 | 30.1 | 31.7 | 35.2 | 35.0 |

Table 16 (below) describes the biochemical status of Subject No. 3. The first column represents the status of the subject prior to treatment with the plant extract. Columns 2 and 3 show data from biochemical tests during treatment and at the end of treatment, respectively. The fourth and fifth columns list the measurement units and the normal values, respectively. All of the data for the biochemical tests was within the range of normal values. In addition, all of the data reflects increases, except for the HDL and phosphorus.

TABLE 16

| Biochemical Tests | Oct 16 1992 | Nov 9 1992 | Nov 16 1992 | Units | Normal Values |
|---|---|---|---|---|---|
| Urea | 30 | 25 | 38 | mg/100 ml | 15–55 |
| Cholesterol | 141 | 174 | 191 | " | 125–260 |
| HDL | 42 | 36 | 34 | " | 30–65 |

TABLE 16-continued

| Biochemical Tests | Oct 16 1992 | Nov 9 1992 | Nov 16 1992 | Units | Normal Values |
|---|---|---|---|---|---|
| LDL | 92 | 116 | 132 | " | 88–188 |
| Triglycerides | 86 | 112 | 111 | " | 40–160 |
| Creatinine | 1.0 | 1.2 | 1.3 | " | 0.9–1.5 |
| Calcium | 8.7 | 8.7 | 9.4 | " | 8.1–10.4 |
| Phosphorus | 3.5 | 3.1 | 3.2 | " | 2.5–4.5 |
| Magnesium | 1.8 | 1.9 | 2.0 | mEq/1 | 1.7–2.4 |

Table 17 (below) shows changes in the blood electrolytes of Subject No. 3. All values were measured in mEq/l. The first column reflects the results before treatment with the plant extract. The second and third columns represent during and the end of treatment, respectively. The fourth column shows the range of normal values. All of the data showed values within the range of normal values. The potassium and sodium electrolytes showed an increase during the treatment but a decrease at the end of the treatment. All the remaining electrolytes reflected a decrease as a result of the treatment.

TABLE 17

| Electrolytes | Oct 16 1992 | Nov 9 1992 | Nov 16 1992 | Normal Values |
|---|---|---|---|---|
| K | 4.3 | 4.6 | 4.1 | 3.5–5.1 |
| Na | 136 | 137 | 142 | 136–146 |
| Cl | 105 | 99 | 102 | 98–107 |
| Trans-GO | 32 | 17 | 17 | 5–40 |
| Transam-GP | 42 | 12 | 12 | 5–40 |
| γ-GT | 48 | 13 | 22 | 10–50 |
| Alp | 64 | 57 | 59 | 30–125 |

Table 18 (below) demonstrates the results of electrophoresis. The first column shows the results prior to treatment with the plant extract. The second column shows the results during the treatment, and the third column reflects the results at the end of the treatment. The fourth column shows the range of normal values. All the data was within the range of normal values and showed an increase, except for the gamma and albumin/globulin ratio.

TABLE 18

| Protein Electrophoresis | OCT 16 1992 | NOV 9 1992 | NOV 16 1992 | Normal Values |
|---|---|---|---|---|
| Alb | 45 | 46.3 | 45.4 | 52–65 |
| a1 | 2.5 | 3.1 | 3.2 | 2–4.5 |
| a2 | 9.9 | 12.3 | 12.5 | 11–15 |
| β | 10.7 | 9.6 | 10.8 | 6–13 |
| γ | 31.9 | 28.7 | 28.1 | 10–19 |
| Alb/Glob | 0.82 | 0.86 | 0.83 | |

SUBJECT NO. 4

Subject No. 4, along with subjects 5 through 9, was diagnosed HIV positive but tested negative for the HIV antigen at both the beginning and end of the treatment. Subject No. 4 was apparently not taking any drugs, including AZT. Subject No. 4 was treated from Oct. 15, 1992 to Nov. 9, 1992. Blood for the Oct. 15, 1992 tests was taken prior to treatment and blood for the Nov. 9, 1992 test was taken after treatment.

Table 19 (below) reveals that Subject No. 4 tested negative for HIV-AG before and after the treatment with the plant extract. The T-3 and T-8 cells increased significantly as a result of the treatment.

TABLE 19

| HIV-AG<br>T CELLS | OCT<br>12<br>1992<br>NEGATIVE | OCT<br>27<br>1992 | NOV<br>9<br>1992<br>NEGATIVE |
|---|---|---|---|
| ANL % | 25 | 21 | 23 |
| ANL | 600 | 525 | 563 |
| T3 | 200 | 378 | 309 |
| T3% | 80 | 72 | 55 |
| T4 | 42.5 | 21 | 23 |
| T4% | 17 | 4 | 4 |
| T8 | 152 | 346 | 261 |
| T8% | 61 | 66 | 44 |

Table 20 (below) discloses specific changes in white blood cell types of Subject No. 4 before treatment with the plant extract. The first 3 columns show the test results prior to treatment. The next four columns represent the changes in the white blood cells during the treatment. As shown in table 20, the monocytes significantly increased by the end of treatment. The neutrophils increased during the middle of the treatment but remained approximately 8 then decreased by the end of the treatment. The lymphocytes remained approximately the same.

TABLE 20

| | Oct 12 1992 | Oct 14 1992 | Oct 15 1992 | Oct 21 1992 | Oct 27 1992 | Nov 2 1992 | Nov 9 1992 |
|---|---|---|---|---|---|---|---|
| WBC TYPES | | | | | | | |
| Lymphocytes | 10 | 23 | 25 | 22 | 21 | 23 | 18 |
| Monocytes | 13 | 3 | 10 | 12 | 4 | 9 | 58 |
| Eosinophils | 20 | — | 2 | — | — | — | — |
| Basophils | — | — | — | — | — | — | — |
| Neutrophils | 57 | 74 | 63 | 66 | 75 | 68 | 24 |

Table 21 (below) shows various blood test results taken before, during, and at the end of the treatment with the plant extract. The first three columns represent tests taken before treatment with the plant extract. Columns four to seven represent tests taken after treatment, and the last two columns represent the range of normal values and the unit measurement. Most of the data showed an increase. The MCHC, PLT, and LYN% increased during the treatment but decreased or remained the same by the end of the treatment. The MCV, MCH, NEUT%, and NEUT data showed a decrease.

TABLE 21

| | Oct 12 1992 | Oct 14 1992 | Oct 15 1992 | Oct 21 1992 | Oct 27 1992 | Nov 2 1992 | Nov 9 1992 | Normal | Units |
|---|---|---|---|---|---|---|---|---|---|
| Blood Cells | | | | | | | | | |
| WBC | 2.5 | 2.5 | 2.4 | 2.6 | 2.5 | 3.6 | 3.3 | 4.8–10.8 | K/ul |
| RBC | 3.8 | 3.98 | 3.93 | 3.87 | 3.95 | 4.22 | 4.12 | 4.4–5.8 | M/ul |
| HNb | 8.7 | 8.9 | 9.0 | 8.9 | 8.9 | 9.4 | 8.9 | 13.9–17.5 | g/dl |
| HCT | 28.1 | 29.2 | 28.7 | 27.8 | 28.2 | 30.1 | 28.7 | 42.0–52.5 | % |
| MCV | 73.9 | 73.4 | 73.0 | 71.8 | 71.4 | 71.3 | 69.7 | 80.5–98.5 | fl |
| MCH | 22.9 | 22.4 | 22.9 | 23.0 | 22.5 | 22.3 | 21.6 | 25.5–34.5 | pg |
| MCHC | 31.0 | 30.5 | 31.4 | 32.0 | 31.6 | 31.2 | 31.0 | 31.5–36.5 | pg |
| PLT | 464.0 | 481 | 207 | 480 | 215 | 492 | 192 | 150–350 | K/ul |
| LYM % | 20.6 | 23.5 | 23.0 | 22.1 | 23.0 | 21.0 | 18.0 | 20–45 | % |
| MID % | 52.2 | 2.8 | — | — | — | — | 58.3 | 1–15 | % |
| NEUT % | 27.2 | 73.7 | — | — | — | — | 23.7 | 45–80 | % |
| LYM | 0.5 | 0.6 | 0.6 | 0.6 | 0.6 | 0.8 | 0.6 | 1.0–4.0 | K/ul |
| MID | 1.3 | 0.1 | — | — | — | — | 1.9 | 0–1 | K/ul |
| NEUT | 0.7 | 1.8 | — | — | — | — | 0.8 | 2.6–9.0 | K/ul |
| RDW-CV | 15.1 | 15.6 | 16.0 | 15.8 | 16.2 | 16.0 | 15.3 | 11.0–16.0 | % |
| PDW | — | — | — | — | — | — | — | 9.0–17.0 | $ |
| MPV | — | — | — | — | — | — | — | 9.0–13.0 | fl |
| P-LCR | — | — | — | — | — | — | — | 13–43 | % |

Table 22 (below) describes the biochemical status of Subject No. 4. The first column represents the status of the subject prior to treatment with the plant extract. Columns 2 and 3 show data for biochemical tests taken during treatment and at the end of treatment, respectively. The fourth and fifth columns list the measurement units and the range of normal values, respectively. The data from the tests showed that the cholesterol and triglycerides increased, with the highest value of the triglycerides being in the middle of the treatment. All other biochemical tests were within the range of normal values, except for the HDL and triglycerides.

TABLE 22

| Biochemical Tests | Oct 12 1992 | Oct 27 1992 | Nov 9 1992 | Units | Normal Values |
|---|---|---|---|---|---|
| Urea | 36 | 34 | 36 | mg/100 ml | 15–55 |
| Cholesterol | 87 | 100 | 102 | " | 125–260 |
| HDL | 29 | 34 | 29 | " | 30–65 |
| LDL | 52 | 62 | 51 | " | 88–188 |
| Triglycerides | 152 | 312 | 212 | " | 40–160 |
| Creatinine | 1.2 | 1.0 | 1.2 | " | 0.9–1.5 |
| Calcium | — | 9.8 | 8.8 | " | 8.1–10.4 |
| Phosphorus | — | 3.4 | 2.9 | " | 2.5–4.5 |
| Magnesium | — | 1.9 | 1.8 | mEq/1 | 1.7–2.4 |

Table 23 (below) shows changes in the blood electrolytes of Subject No. 4. All values were measured in mEq/l. The first column reflects the results before treatment with the plant extract. The second and third columns represent during and the end of the treatment, respectively. The fourth column shoes the range of normal values. As shown in table 23, all data was within the range of normal values by the end of the treatment. Also, there was an increase in the sodium, gamma-GT, and Alp electrolytes.

TABLE 23

| Electrolytes | OCT 12 1992 | OCT 27 1992 | NOV 9 1992 | Normal Values |
|---|---|---|---|---|
| K | — | 5.2 | 5.0 | 3.5–5.1 |
| Na | — | 134 | 140 | 136–146 |
| Cl | — | 103 | 102 | 98–107 |
| Trans-Go | 35 | 29 | 23 | 5–40 |
| Trans-GP | 18 | 17 | 18 | 5–40 |
| γ-GT | 12 | 16 | 22 | 10–50 |
| Alp | 63 | 89 | 84 | 30–125 |

Table 24 (below) reflects the results of protein electrophoresis. The first column shows the results prior to treatment with the plant extract. The second column reflects the results during treatment. The third column shows the results at the end of the treatment. The fourth column shows the range of normal values. As indicated by the table, all the values were outside of the normal range by the end of the treatment, except for the a1 data. Moreover, the only increases in data were in the a2 and gamma data.

TABLE 24

| Protein Electrophoresis | OCT 12 1992 | OCT 27 1992 | NOV 9 1992 | Normal Values |
|---|---|---|---|---|
| ALBUMIN | 45.4 | 43.9 | 42.3 | 52–65 |
| a1 | 3.5 | 3.3 | 3.3 | 2–4.5 |
| a2 | 9.4 | 10.1 | 10.7 | 11–15 |

TABLE 24-continued

| Protein Electrophoresis | OCT 12 1992 | OCT 27 1992 | NOV 9 1992 | Normal Values |
|---|---|---|---|---|
| β | 14.4 | 12.1 | 13.1 | 6–13 |
| γ | 24.3 | 30.6 | 30.6 | 10–19 |
| Alb/Glob[2] | 0.83 | 0.78 | 0.73 | |

[2]Ratio between Albumin to Globulin

SUBJECT NO. 5

Subject No. 5 was also from the HIV positive asymptomatic group and was taking AZT before treatment with the plant extract. Subject No. 5 was treated from Oct. 21, 1992 to Nov. 9, 1992. Blood for the Oct. 21, 1992 tests was taken prior to treatment and blood for the Nov. 9, 1992 test was taken after treatment. The same tests were performed on Subject No. 5 as were performed on the previous subjects. Moreover, the units for measurement, as well as the standard values, are the same as those used for the preceding subjects.

Table 25 (below) shows the results of the HIV-AG and T-cell tests. Subject No. 5 had a negative HIV-AG before and after treatment, and a negative HIV-AG after less than one month of treatment. The T-3 and T-8 cells increased significantly over the course of the treatment.

TABLE 25

| HIV T CELLS | Oct 21 1992 NEGATIVE | Nov 9 1992 NEGATIVE |
|---|---|---|
| ANL % | 32 | 43 |
| ANL | 1312 | 1548 |
| T3% | 82 | 93 |
| T3 | 1075 | 1439 |
| T4% | 7.5 | 8 |
| T4 | 98 | 123 |
| T8% | 72 | 84 |
| T8 | 944 | 1300 |

Table 26 (below) represents changes in the white blood cell types of Subject No. 5 before treatment with the plant extract. The first two columns show the test results before treatment. The next two columns represent the changes of white blood cells during the treatment. As shown in the table, the lymphocytes and monocytes increased as a result of the treatment, whereas the neutrophils decreased.

TABLE 26

| WBC TYPES | Oct 19 1992 | Oct 21 1992 | Nov 5 1992 | Nov 9 1992 |
|---|---|---|---|---|
| Lymphocytes | 28 | 32 | 40 | 43 |
| Monocytes | 1 | 9 | 11 | 12 |
| Eosinophills | — | — | — | — |
| Basophills | — | — | — | — |
| Neutrophils | 71 | 59 | 49 | 45 |

Table 27 (below) shows various blood test results taken before, during, and at the end of the treatment with the plant extract. The first two columns represent tests taken before treatment. Columns three and four represent tests taken after treatment. As indicated in table 27, there was an overall increase in most types of blood cells with only a few exceptions. The white blood cells, PLT, NEUT%, NEUT, and RDW-CV decreased, while the MCHC and MID remained approximately the same.

TABLE 27

| Blood Cells | Oct 9 1992 | Oct 21 1992 | Nov 5 1992 | Nov 9 1992 |
|---|---|---|---|---|
| WBC | 6.0 | 4.1 | 4.7 | 3.6 |
| RBC | 2.98 | 3.01 | 3.35 | 3.47 |
| Hb | 11.4 | 11.5 | 13.0 | 13.3 |
| HCT | 33.9 | 34.3 | 38.2 | 39.6 |
| MCV | 113.8 | 114.0 | 114.0 | 114.0 |
| MCH | 38.3 | 38.2 | 38.8 | 38.3 |
| MCHC | 33.6 | 33.5 | 34.0 | 33.6 |
| PLT | 245 | 221 | 220 | 219 |
| LYM % | 28.5 | 31.9 | 37.9 | 43.0 |
| MID % | 2.3 | 9.2 | — | 12.3 |
| NEUT % | 69.2 | 58.9 | — | 44.7 |
| LYM | 1.7 | 1.3 | 1.8 | 1.5 |
| MID | 0.1 | 0.4 | — | 0.4 |
| NEUT | 4.2 | 2.4 | — | 1.7 |
| RDW-CV | 12.5 | 12.5 | 11.3 | 12.4 |
| PDW | 13.3 | 11.9 | 13.2 | 14.5 |
| MPV | 10.4 | 10.3 | 10.4 | 10.8 |
| P-LCR | 28.8 | 26.7 | 28.9 | 31.3 |

Table 28 (below) describes the biochemical status of Subject No. 5. The first column represents the status of the subject prior to treatment with the plant extract. The second column reflects the data from the biochemical tests at the end of the treatment. The third and fourth columns show the range of normal values and the measurement units, respectively. As indicated by the table, the data is generally within the range of normal values and reflects increases only in the tests for urea, HDL, and magnesium.

TABLE 28

| Biochemical Tests | Oct 21 1992 | Nov 9 1992 | Normal Values | Units |
|---|---|---|---|---|
| Urea | 24 | 26 | 15–55 | mg/1000 ml |
| Cholesterol | 192 | 160 | 125–260 | " |
| HDL | 31 | 33 | 30–65 | " |
| LDL | 129 | 98 | 88–188 | " |
| Triglycerides | 161 | 149 | 40–160 | " |
| Creatinine | 1.0 | 1.0 | 0.9–1.5 | " |
| Calcium | 9.5 | 9.2 | 8.1–10.4 | " |
| Phosphorus | 3.6 | 3.6 | 2.5–4.5 | " |
| Magnesium | 1.9 | 2.1 | 1.7–2.4 | mEq/l |

Table 29 (below) shows changes in the blood electrolytes of Subject No. 5. All values are measured in mEq/l. The first column reflects the results prior to treatment with the plant extract. The second column represents the end of the treatment. The third column shows the range of normal values. All the data is within the range of normal values. Moreover, the data reflects an increase in potassium, sodium, trans-GP, and alp electrolytes.

TABLE 29

| Electrolytes | Oct 21 1992 | Nov 9 1992 | Normal Values |
|---|---|---|---|
| K | 4.1 | 4.9 | 3.5–51 |
| Na | 131 | 142 | 136–146 |
| Cl | 105 | 103 | 98–107 |
| Trans-GO | 27 | 23 | 5–40 |
| Trans-GP | 31 | 32 | 5–40 |

TABLE 29-continued

| Electrolytes | Oct 21 1992 | Nov 9 1992 | Normal Values |
|---|---|---|---|
| γ-GT | 31 | 30 | 10–50 |
| Alp | 77 | 90 | 30–125 |

Table 30 (below) demonstrates the results of protein electrophoresis. The first column shows the results prior to treatment with the plant extract. The second column reflects the results at the end of treatment. The third column shows the range of normal values. All of the data was within the range of normal values. There was an increase in the data for the beta, gamma, and albumin/globulin ratio.

TABLE 30

| Protein Electrophoresis | Oct 21 1992 | Nov 9 1992 | Normal Values |
|---|---|---|---|
| Alb | 59.7 | 59.3 | 52–65 |
| a1 | 3.0 | 3.0 | 2–4.5 |
| a2 | 11.3 | 11.0 | 11–15 |
| β | 10.3 | 10.9 | 6–13 |
| γ | 15.7 | 15.8 | 10–19 |
| Alb/Glob | 1.48 | 1.46 | |

SUBJECT NO. 6

Subject No. 6 belonged to the HIV positive and asymptomatic group. Subject No. 6 was taking AZT up until a few days prior to treatment with the plant extract. Subject No. 6 was treated from Oct. 19, 1992 to Nov. 18, 1992. Blood for the Oct. 19, 1992 test was taken prior to treatment and blood for the Nov. 18, 1992 test was taken after treatment. The same tests were performed on Subject No. 6 as were performed on the previous subjects. The units for measurement, as well as the standard values, are the same as with the previous subjects.

Table 31 (below) shows the results of the HIV-AG and T-cell tests. Subject No. 6 showed a negative HIV-AG before and after treatment. The T-cells showed no significant change.

TABLE 31

| HIV-AG T-CELLS | Oct 19 1992 NEGATIVE | Oct 29 1992 | Nov 18 1992 NEGATIVE |
|---|---|---|---|
| ANL % | 24 | 26 | 27 |
| ANL | 1656 | — | — |
| T3% | 72 | 71 | 72 |
| T3 | 1192 | — | — |
| T4% | 4 | 4 | 3 |
| T4 | 66 | — | — |
| T8% | 67 | 66 | 65 |
| T8 | 1109 | — | — |

Table 32 (below) represents specific changes in the white blood cell types of Subject No. 6 before treatment with the plant extract. The first three columns show the test results prior to treatment. The next four columns represent the changes in white blood cells during the treatment. As shown in the table, the overall number of lymphocytes decreased, while the monocytes increased and the neutrophils remained approximately the same.

TABLE 32

| | Oct 15 1992 | Oct 16 1992 | Oct 19 1992 | Oct 24 1992 | Oct 29 1992 | Nov 4 1992 | Nov 18 1992 |
|---|---|---|---|---|---|---|---|
| WBC Types | | | | | | | |
| Lymphocytes | 26 | 28 | 24 | 19 | 26 | 23 | 14 |
| Monocytes | 1 | 4 | 1 | 2 | 4 | 1 | 13 |
| Eosinophils | — | 2 | — | — | 2 | — | — |
| Basophils | — | — | — | — | — | — | — |
| Neutrophils | 73 | 66 | 75 | 79 | 68 | 76 | 73 |

Table 33 (below) shows various blood test results taken before, during, and at the end of the treatment with the plant extract. The first three columns represent tests taken before treatment. Columns four to seven represent tests taken after treatment. As shown in the table, almost all of the blood cell types reflected increases during days 10–20 of the treatment. This increase occurred despite a general decrease in the data by the end of the treatment in many of the blood cells.

TABLE 33

| | Oct 15 1992 | Oct 16 1992 | Oct 19 1992 | Oct 24 1992 | Oct 29 1992 | Nov 4 1992 | Nov 18 1992 |
|---|---|---|---|---|---|---|---|
| Blood Cells | | | | | | | |
| WBC | 8.2 | 7.0 | 6.9 | 7.6 | 8.4 | 8.6 | 6.7 |
| RBC | 3.98 | 3.91 | 3.88 | 3.76 | 4.13 | 4.35 | 3.90 |
| Hb | 12.9 | 12.6 | 12.7 | 12.0 | 13.4 | 14.3 | 12.6 |
| HCT | 38.8 | 38.3 | 37.8 | 36.9 | 40.8 | 42.5 | 37.7 |
| CV | 97.5 | 98.0 | 97.4 | 98.1 | 98.8 | 97.7 | 96.7 |
| MCH | 32.4 | 32.2 | 32.7 | 31.9 | 32.4 | 32.9 | 32.3 |
| MCHC | 33.2 | 32.9 | 33.6 | 32.5 | 32.8 | 33.6 | 33.4 |
| PLT | 159 | 153 | 133 | 110 | 186 | 146 | 178 |
| LYM % | 26.3 | 28.7 | 24.5 | 18.9 | 26.7 | 23.5 | 14.0 |
| MID % | 2.7 | 7.2 | 2.9 | 2.4 | 7.5 | 2.7 | 13.1 |
| NEUT % | 71.0 | 64.1 | 72.6 | 78.7 | 65.8 | 73.8 | 72.9 |
| LYM | 2.2 | 2.0 | 1.7 | 1.4 | 2.2 | 2.0 | 0.9 |
| MID | 0.2 | 0.5 | 0.2 | 0.2 | 0.6 | 0.2 | 0.9 |
| NEUT | 5.8 | 4.5 | 5.0 | 6.0 | 5.6 | 6.4 | 4.9 |
| RDW-CV | 12.5 | 12.1 | 12.8 | 12.4 | 13.0 | 13.5 | 13.3 |
| PDW | 13.0 | 12.9 | 13.8 | 14.3 | 13.0 | 14.5 | 11.4 |
| MPV | 10.4 | 10.5 | 10.4 | 11.5 | 10.1 | 11.0 | 9.8 |
| P-LCR | 29.3 | 28.5 | 28.7 | 38.4 | 26.6 | 33.1 | 23.7 |

Table 34 (below) describes the biochemical status of Subject No. 6. The first column represents the status of the subject prior to treatment with the plant extract. Columns two and three reflect data from biochemical tests during and at the end of treatment, respectively. The fourth and fifth columns show the measurement units and the range of normal values for each biochemical test, respectively. As the table shows, the data for the urea and cholesterol tests increased and was especially high during the middle of the treatment. Likewise, the data for the LDL, creatinine, and calcium tests was particularly high during the middle of the treatment. The data for the HDL, triglycerides, calcium, and phosphorus showed a decrease by the end of the treatment.

TABLE 34

| Biochemical Tests | Oct 19 1992 | Oct 29 1992 | Nov 18 1992 | Units | Normal Values |
|---|---|---|---|---|---|
| Urea | 23 | 49 | 28 | mg/100 ml | 15–55 |
| Cholesterol | 208 | 328 | 216 | " | 125–260 |
| HDL | 29 | 28 | 25 | " | 30–65 |

TABLE 34-continued

| Biochemical Tests | Oct 19 1992 | Oct 29 1992 | Nov 18 1992 | Units | Normal Values |
|---|---|---|---|---|---|
| LDL | 131 | 228 | 131 | " | 88–188 |
| Triglycerides | 341 | 331 | 301 | " | 40–160 |
| Creatinine | 0.9 | 1.4 | 0.9 | " | 0.9–1.5 |
| Calcium | 8.8 | 9.2 | 8.4 | " | 8.1–10.4 |
| Phosphorus | 4.2 | 3.8 | 3.6 | " | 2.5–4.5 |
| Magnesium | 2.0 | 2.0 | 2.0 | mEq/1 | 1.7–2.4 |

Table 35 (below) shows changes in the blood electrolytes of Subject No. 6. All values were measured in mEq/l. The first column shows the results prior to treatment with the plant extract. The second and third columns represent during and the end of treatment, respectively. The fourth column shows the range of normal values. As the table shows, all of the data is within the range of normal values, except for the alp data which is only within the range during the middle of treatment. Furthermore, there was an increase in the data during the middle of treatment for the potassium electrolytes, and both during and at the end of treatment as a shown by the trans-GP, gamma-GT, and alp data.

TABLE 35

| | Oct 10 1992 | Oct 29 1992 | Nov 18 1992 | Normal |
|---|---|---|---|---|
| K | 4.4 | 4.2 | 4.5 | 3.5–5.1 |
| Na | 137 | 134 | 133 | 136–146 |
| Cl | 104 | 98 | 101 | 98–10.7 |
| Trans-GO | 28.2 | 28.0 | 28.1 | 5–40 |
| Trans-GP | 16.1 | 27.0 | 20.5 | 5–40 |
| γ-GT | 15.48 | 23 | 12.71 | 10–50 |
| Alp | 28.0 | 32 | 29.7 | 30–125 |

Table 36 (below) represents the results of protein electrophoresis. Column 1 shows the results before treatment. Column two shows the results during the treatment, and column three shows the results at the end of the treatment. The fourth column shows the range of normal values. As the table indicates, only the a1 and a2 data is within the range of normal values. Moreover, the table shows that there was an overall increase in the a1, a2, beta, and gamma data.

TABLE 36

| Protein Electrophoresis | Oct 19 1992 | Oct 29 1992 | Nov 18 1992 | Normal Values |
|---|---|---|---|---|
| Alb | 43.2 | 42.3 | 39.4 | 52–65 |
| a1 | 2.8 | 3.0 | 3.3 | 2–4.5 |
| a2 | 10.2 | 11.5 | 11.2 | 11–15 |
| β | 13.2 | 13.0 | 14.4 | 6–13 |
| γ | 30.6 | 30.2 | 31.7 | 10–19 |
| Alb/Glob | 0.76 | 0.73 | 0.65 | |

SUBJECT NO. 7

Subject No. 7 was taking AZT prior to treatment with the plant extract. Subject No. 7 was treated from Oct. 15, 1992 to Nov. 9, 1992. Blood for the Oct. 15, 1992 tests was taken prior to treatment, and blood for the Nov. 9, 1992 test was taken after treatment. The same tests were performed on Subject No. 7 as with the previous subjects. Likewise, the units for measurement, as well as the standard values, are the same for Subject No. 7 as with the previous subjects.

Table 37 (below) shows the results of the HIV-AG and T-Cell tests. Subject No. 7 tested negative for HIV-AG before and after treatment. As the table indicates, the number of T-cells decreased by the end of the treatment.

TABLE 37

| HIV-AG T-CELLS | Oct 15 1992 NEGATIVE | Oct 29 1992 | Nov 9 1992 NEGATIVE |
|---|---|---|---|
| ANL % | 19 | 19 | 17 |
| ANL | 627 | — | — |
| T3% | 69 | 71 | 62 |
| T3 | 432 | — | 379 |
| T4% | 8 | 5 | 4 |
| T4 | 50 | — | 24 |
| T8% | 58 | 62 | 50 |
| T8 | 363 | — | 306 |

Table 38 (below) represents specific changes in the white blood cell types of Subject No. 7 before treatment with the plant extract. The first three columns are the test results before treatment. The next three columns represent the changes in white blood cells during the treatment. As shown in table 38, there was an overall decrease in the lymphocytes and monocytes. In contrast, there was an increase in the neutrophils.

TABLE 38

| WBC Types | Oct 13 1992 | Oct 14 1992 | Oct 15 1992 | Oct 21 1992 | Oct 29 1992 | Nov 9 1992 |
|---|---|---|---|---|---|---|
| Lymphocytes | 20 | 20 | 19 | 17 | 19 | 17 |
| Monocytes | 12 | 13 | 9 | 14 | 7 | 8 |
| Eosinophils | — | — | 5 | — | — | — |
| Basophils | — | — | — | — | — | — |
| Neutrophils | 68 | 67 | 67 | 69 | 74 | 75 |

Table 39 (below) shows various blood test results taken before, during, and at the end of the treatment with the plant extract. The first three columns represent tests taken before treatment, while the remaining columns represent tests taken after treatment. As the table shows, most of the blood cells increased as a result of the treatment and included the greatest increases generally during the middle of the treatment.

TABLE 39

| DATES | Oct. 13 1992 | Oct. 14 1992 | Oct. 15 1992 | Oct. 21 1992 | Oct. 29 1992 | Nov. 9 1992 |
|---|---|---|---|---|---|---|
| Blood Cells | | | | | | |
| WBC | 2.9 | 3.3 | 3.3 | 3.4 | 4.7 | 3.6 |
| RBC | 4.31 | 4.34 | 4.24 | 4.29 | 4.35 | 4.41 |
| Hb | 12.0 | 12.3 | 12.0 | 12.0 | 12.3 | 13.0 |
| HCT | 38.1 | 38.3 | 37.5 | 37.3 | 37.8 | 39.4 |
| MCV | 88.4 | 88.2 | 88.4 | 86.9 | 86.9 | 89.3 |
| MCH | 27.8 | 28.3 | 28.3 | 28.0 | 28.3 | 29.5 |
| MCHC | 31.5 | 32.1 | 32.0 | 32.2 | 32.5 | 33.0 |
| PLT | 98 | 111 | 97 | 102 | 149 | 141 |
| LYM % | 19.9 | 19.9 | 15.4 | 17.0 | 19.0 | 16.8 |
| MID % | 12.4 | 13.5 | — | 13.7 | 7.3 | 8.2 |
| NEUT % | 67.7 | 66.6 | — | 69.3 | 73.7 | 75.0 |
| LYM | 0.6 | 0.7 | 0.5 | 0.6 | 0.9 | 0.6 |
| MID | 0.4 | 0.4 | — | 0.5 | 0.3 | 0.3 |
| NEUT | 1.9 | 2.2 | — | 2.3 | 3.5 | 2.7 |

TABLE 39-continued

| DATES | Oct. 13 1992 | Oct. 14 1992 | Oct. 15 1992 | Oct. 21 1992 | Oct. 29 1992 | Nov. 9 1992 |
|---|---|---|---|---|---|---|
| RDW-CV | 15.0 | 14.1 | 15.1 | 14.3 | 14.4 | 15.5 |
| PDW | 25.3 | — | 20.7 | — | 25.7 | — |
| MPV | 13.5 | — | 13.7 | — | 13.6 | — |
| P-LCR | 52.3 | — | 53.8 | — | 52.7 | — |

Table 40 (below) describes the biochemical status of Subject No. 7. The first column reflects the test data from the subject prior to treatment with the plant extract. Columns two and three show the data from biochemical tests taken during and at the end of treatment, respectively. The fourth and fifth columns list the measurement units and the range of normal values, respectively. As shown in table 40, the data was within the range of normal values by the end of the treatment. Moreover, there was an overall increase in the data, with the exception of the triglycerides, creatinine, and calcium.

TABLE 40

| Biochemical Tests | Oct 15 1992 | Oct 29 1992 | Nov 9 1992 | Units | Normal Values |
|---|---|---|---|---|---|
| Urea | 47 | 36 | 52 | mg/ml | 15–55 |
| Cholesterol | 142 | 142 | 158 | " | 125–260 |
| HDL | 24 | 24 | 30 | " | 30–65 |
| LDL | 82 | 92 | 105 | " | 88–188 |
| Triglycerides | 210 | 207 | 116 | " | 40–160 |
| Creatinine | 1.2 | 1.2 | 1.1 | " | 0.9–1.5 |
| Calcium | 9.7 | 8.9 | 9.2 | " | 8.1–10.4 |
| Phosphorus | 3.9 | 4.0 | 4.1 | " | 2.5–4.5 |
| Magnesium | 2.0 | 1.9 | 2.1 | mEq/l | 1.7–2.4 |

Table 41 (below) shows changes in the blood electrolytes of Subject No. 7. All values are measured in mEq/l. The first column shows the results before treatment with the plant extract. The second and third columns represent the during and end of treatment, respectively. The fourth column shows the range of normal values. Subsequent to treatment, all data was within the normal range of values, except for the gamma-GT data. Moreover, there was an overall increase in the data for the sodium, trans-GO, trans-GP, and gamma-GT by the end of the treatment.

TABLE 41

| Electrolytes | Oct 15 1992 | Oct 29 1992 | Nov 9 1992 | Normal Values |
|---|---|---|---|---|
| K | 5.6 | 4.3 | 4.2 | 3.5–5.1 |
| Na | 108 | 140 | 138 | 136–146 |
| Cl | 102 | 101 | 101 | 98–107 |
| Trans-GO | 27 | 28 | 28 | 5–40 |
| Trans-GP | 17 | 27 | 22 | 5–40 |
| γ-GT | 48 | 20 | 61 | 10–50 |
| Alp | 97 | 88 | 86 | 30–125 |

Table 42 (below) shows the results of protein electrophoresis. The first column shows the results prior to treatment with the plant extract. The second column shows the results during the treatment and the third column shows the results at the end of the treatment. The fourth column shows the range of normal values. As the table indicates, the data was within the range of normal values. Furthermore, there was an overall increase in the albumins, a1 data, a2 data, beta data, and albumin/globulin ratio.

TABLE 42

| Protein Electrophoresis | Oct 15 1992 | Oct 29 1992 | NOV 9 1992 | Normal Values |
|---|---|---|---|---|
| Albumins | 59.4 | 61.2 | 59.9 | 52–65 |
| a1 | 2.5 | 2.4 | 2.8 | 2–4.8 |
| a2 | 11.0 | 11.5 | 11.1 | 11–15 |
| β | 11.1 | 10.8 | 12.2 | 6–13 |
| γ | 16.0 | 14.1 | 14 | 10–19 |
| Alb/Glob | 1.46 | 1.58 | 1.49 | |

SUBJECT NO. 8

Subject No. 8 was not taking any AZT or DDI but was ingesting some herbal remedies such as, for example, gingseng. Subject No. 8 was treated from Oct. 21, 1992 to Nov. 16, 1992. Blood for the Oct. 21, 1992 tests was taken prior to treatment and blood for the Nov. 11, 1992 tests was taken after treatment. The same tests were performed on Subject No. 8 as on the previous subjects. The units for measurement, as well as the standard values, are the same with Subject No. 8 as for the previous subjects.

Table No. 43 (below) shows the results of the HIV-AG and T-Cell tests. Subject No. 8 tested negative for HIV-AG before and after treatment. The T4 cells increased significantly due to treatment.

TABLE 43

| HIV-AG T-CELLS | OCT 21 1992 NEGATIVE | NOV 3 1992 | NOV 16 1992 NEGATIVE |
|---|---|---|---|
| ANL % | 56 | 49 | 48 |
| ANL | 2360 | — | 2400 |
| T3% | 83 | 86 | 79 |
| T3 | 1900 | — | 1896 |
| T4% | 25 | 36 | 31 |
| T4 | 575 | — | 744 |
| T8% | 53 | 48 | 47 |
| T8 | 1219 | — | 1128 |

Table 44 (below) represents specific changes in the white blood cell types prior to treatment with the plant extract. The first three columns reflect the test results before treatment. The next four columns represent the changes in the White blood cells during treatment. As shown in the table, the neutrophils increased while the lymphocytes and monocytes remained approximately the same.

TABLE 44

| WBC TYPES | Oct 19 1992 | Oct 21 1992 | Oct 26 1992 | Nov 3 1992 | Nov 12 1992 | Nov 16 1992 |
|---|---|---|---|---|---|---|
| Lymphocytes | 51 | 56 | 28 | 45 | 49 | 48 |
| Monocytes | 10 | 12 | 5 | 11 | 9 | 8 |
| Eosinophils | — | — | 2 | — | — | — |
| Basophils | — | — | — | — | — | — |
| Neutrophils | 39 | 32 | 5 | 44 | 42 | 44 |

Table 45 (below) shows various blood test results taken before, during, and at the end of the treatment with the plant extract. The first three columns represent tests taken before treatment. Columns four to six represent tests taken after treatment. As shown in the table, there was an overall increase in the RBC, HNb, HCT, PLT, NEUT%, and NEUT data, with the most significant increases often being during days 10–20 of treatment. Likewise, the data for the MCV, MCH, MCHC, MID%, LYM, and MID remained approximately the same but did include increases during days 10–20 of treatment. Furthermore, there was a decrease in the LYM% and RDW-CV data.

TABLE 45

| Blood Cells | Oct 19 1992 | Oct 21 1992 | Oct 26 1992 | Nov 3 1992 | Nov 9 1992 | Nov 16 1992 |
|---|---|---|---|---|---|---|
| WBC | 4.8 | 4.2 | 7.1 | 4.5 | 5.9 | 5.0 |
| RBC | 6.48 | 6.47 | 6.54 | 6.19 | 6.57 | 6.61 |
| HNb | 12.5 | 12.7 | 12.7 | 12.3 | 13.0 | 12.9 |
| HCT | 39.7 | 39.5 | 39.7 | 37.6 | 39.6 | 40.1 |
| MCV | 61.3 | 61.1 | 60.7 | 60.7 | 60.3 | 60.7 |
| MCH | 19.4 | 19.9 | 19.4 | 19.9 | 19.8 | 19.5 |
| MCHC | 31.5 | 32.2 | 32.0 | 32.7 | 32.8 | 32.2 |
| PLT | 259 | 251 | 265 | 321 | 346 | 282 |
| LYM % | 51.2 | 55.6 | 28.2 | 45.3 | 48.6 | 48.3 |
| MID % | 10.5 | 12.0 | 7.9 | 11.1 | 9.3 | 8.1 |
| NEUT % | 38.3 | 32.4 | 63.9 | 43.6 | 42.1 | 43.6 |
| LYM | 2.5 | 2.3 | 2.0 | 2.0 | 2.9 | 2.4 |
| MID | 0.5 | 0.5 | 0.5 | 0.5 | 0.5 | 0.4 |
| NEUT | 1.8 | 1.4 | 2.0 | 2.0 | 2.5 | 2.2 |
| RDW-CV | 16.8 | 16.7 | 15.1 | 15.1 | 15.0 | 15.6 |
| PDW | — | — | — | — | — | — |
| MPV | — | — | — | — | — | — |
| P-LCR | — | — | — | — | — | — |

Table 46 (below) shows the biochemical status of Subject No. 8. The first column represents the status of the subject prior to treatment with the plant extract. Columns two and three show data from the biochemical tests during and at the end of treatment, respectively. The fourth and fifth columns reflect the measurement units and the range of normal values, respectively. As the table shows, most of the data was within the range of normal values at the end of treatment, except for the HDL and triglycerides data which were slightly outside of the range. In addition, increases were reflected in the data for cholesterol, LDL, triglycerides, calcium, and phosphorus.

TABLE 46

| Biochemical Tests | Oct 21 1992 | Nov 3 1992 | Nov 16 1992 | Units | Normal Values |
|---|---|---|---|---|---|
| Urea | 48 | 40 | 36 | mg/100 ml | 15–55 |
| Cholesterol | 141 | 113 | 182 | " | 125–260 |
| HDL | 32 | 17 | 28 | " | 30–65 |
| LDL | 112 | 78 | 126 | " | 88–188 |
| Triglycerides | 135 | 118 | 161 | " | 40–160 |
| Creatinine | 1.5 | 1.0 | 1.4 | " | 0.9–1.5 |
| Calcium | 9.4 | 9.6 | 9.7 | " | 8.1–10.4 |
| Phosphorus | 3.5 | 3.6 | 3.8 | " | 2.5–4.5 |
| Magnesium | 2 | 2.1 | 2.0 | mEq/l | 1.7–2.4 |

Table 47 (below) shows changes in the blood electrolytes of Subject No. 8. All values were measured in mEq/l. In the first column, the data reflects results before treatment with the plant extract. The second and third columns represent during and the end of treatment, respectively. The fourth column reflects the range of normal values. As the table indicates, all the data is within the range of normal values by the end of the treatment. Moreover, there is an increase in the sodium, chlorine, and alp electrolytes.

TABLE 47

| Electrolytes | Oct 21 1992 | Nov 3 1992 | Nov 16 1992 | Normal Values |
|---|---|---|---|---|
| K | 4.4 | 4.5 | 4.3 | 3.5–5.1 |
| Na | 133 | 137 | 144 | 136–146 |
| Cl | 100 | 102 | 103 | 98–107 |
| Trans-GO | 23 | 19 | 22 | 5–40 |
| Trans-GP | 17 | 12 | 12 | 5–40 |
| γ-GT | 23 | 18 | 14 | 10–50 |
| Alp | 51 | 69 | 60 | 30–125 |

Table 48 (below) represents the results of protein electrophoresis. The first column shows the results before treatment with the plant extract, the second column shows the results during treatment, and the third column shows the results at the end of treatment. The fourth column shows the range of normal values. As shown in the table, most of the data shows an overall decrease by the end of treatment, except for the beta and alp data. However, a majority of the data (a1, a2, gamma, and alp) show a significant increase during days 10–20 of the treatment. By the end of treatment, data for a1, a2, and gamma are not within the range of normal values.

TABLE 48

| Protein Electrophoresis | Oct 21 1992 | Nov 3 1992 | Nov 16 1992 | Normal Values |
|---|---|---|---|---|
| Albubines | 54.8 | 50 | 53.6 | 52–65 |
| a1 | 1.6 | 2.5 | 1.8 | 2–4.5 |
| a2 | 6.8 | 9.6 | 7.0 | 11–15 |
| β | 9.3 | 9.4 | 11.0 | 6–13 |
| γ | 27.5 | 28.5 | 26.6 | 10–19 |
| Alb/Glob | 1.21 | 1.00 | 1.16 | — |
| Alp | 51 | 69 | 60 | 30–125 |

SUBJECT NO. 9

Subject No. 9 was HIV positive and asymptomatic. Subject No. 9 was infected by the virus in 1982 and was taking AZT prior to treatment with the plant extract. Subject No. 9 was treated from Oct. 21, 1992 to Nov. 9, 1992. Blood for the Oct. 21, 1992 test was taken prior to treatment and blood for the Nov. 9, 1992 test was taken after treatment. The same tests were performed on Subject No. 9 as were performed on the previous subjects. The units for measurement, as well as the standard values, are the same as with the previous subjects.

Table 49 (below) shows the results of the HIV-AG and T-Cell tests. Subject No. 9 tested negative for HIV-AG before and after treatment with the plant extract. Moreover, the T-3 and T-8 cells increased due to the treatment.

TABLE 49

| HIV T-Cells | Oct 21 1992 Negative | Nov 9 1992 Negative |
|---|---|---|
| ANL % | 27 | 42 |
| ANL | 1539 | 2184 |
| T3 % | 80 | 92 |
| T3 | 1231 | 2009 |
| T4 % | 24 | 26 |
| T4 | 370 | 567 |
| T8 % | 52 | 63 |
| T8 | 800 | 1375 |

Table 50 (below) represents specific changes in the white blood cell types before treatment with the plant extract. The first two columns show the test results before treatment. The next two columns represent the changes in white blood cells during treatment. As shown in the table, the lymphocytes increased while the monocytes and neutrophils decreased. Moreover, the highest increases occurred during days 10–20 of treatment.

TABLE 50

| WBC TYPES | Oct 19 1992 | Oct 21 1992 | Nov 5 1992 | Nov 9 1992 |
|---|---|---|---|---|
| Lymphocytes | 32 | 27 | 46 | 42 |
| Monocytes | 5 | 6 | 3 | 2 |
| Eosinophils | 2 | 2 | — | 1 |
| Basophils | — | — | — | — |
| Neutrophils | 61 | 65 | 51 | 55 |

Table 51 (below) shows various blood tests taken before, during, and at the end of the treatment with the plant extract. The first two columns represent tests taken before treatment. The next two columns represent tests taken after treatment. As shown in the table, most of the blood cell types increased (WBC, RBC, Hb, CT, MCV, MCH, MCHC, PLT, LYM%, LYM), with the highest increases falling within the 10–20 day period of treatment. The data for the PDW, MP, P-LCR remained substantially the same but included large increases during days 10–20 of treatment. Other data included RDW-CV which remained generally unchanged and the MID%, NEUT%, MID, and NEUT data which showed decreases.

TABLE 51

| Blood Cells | Oct 19 1992 | Oct 21 1992 | Nov 5 1992 | Nov 9 1992 |
|---|---|---|---|---|
| WBC | 5.5 | 5.7 | 6.6 | 5.2 |
| RBC | 4.79 | 4.64 | 5.21 | 5.08 |
| Hb | 14.9 | 14.8 | 16.7 | 17.3 |
| CT | 44.9 | 43.6 | 49.4 | 48.3 |
| MCV | 93.7 | 94.0 | 94.8 | 95.1 |
| MCH | 31.1 | 31.9 | 32.1 | 34.1 |
| MCHC | 33.2 | 33.9 | 33.8 | 35.8 |
| PLT | 180 | 188 | 188 | 192 |
| LYM % | 32.9 | 27.8 | 46.5 | 42.2 |
| MID % | 8.2 | 9.3 | 3.0 | 4.5 |
| NEUT % | 58.9 | 62.9 | 50.5 | 53.3 |
| LYM | 1.8 | 1.6 | 3.1 | 2.2 |
| MID | 0.5 | 0.5 | 0.2 | 0.2 |
| NEUT | 3.2 | 3.6 | 3.3 | 2.8 |
| RDW-CV | 11.7 | 12.0 | 11.6 | 11.7 |
| PDW | 14.1 | 13.2 | 15.7 | 13.5 |
| MP | 11.2 | 10.7 | 11.4 | 10.7 |
| P-LCR | 34.9 | 31.6 | 35.8 | 31.5 |

Table 52 (below) describes the biochemical status of Subject No. 9. The first column represents the status of the subject prior to treatment with the plant extract. The second column shows the data from the biochemical tests at the end of treatment. The third and fourth columns list the measurement units and the range of normal values, respectively. As shown in the table, all of the data is within the range of normal values, with the exception of the triglycerides. There was an increase in the cholesterol, HDL, LDL, and triglycerides.

TABLE 52

| Biochemical Tests | Oct 21 1992 | Nov 9 1992 | Units | Normal Values |
|---|---|---|---|---|
| Urea | 23 | 22 | mg/100 ml | 15–55 |
| Cholesterol | 152 | 200 | " | 125–260 |
| HDL | 35 | 41 | " | 30–65 |

TABLE 52-continued

| Biochemical Tests | Oct 21 1992 | Nov 9 1992 | Units | Normal Values |
|---|---|---|---|---|
| LDL | 110 | 125 | " | 88–188 |
| Triglycerides | 164 | 170 | " | 40–160 |
| Creatinine | 1.0 | 1.0 | " | 0.9–1.5 |
| Calcium | 9.7 | 9.2 | " | 8.1–10.4 |
| Phosphorus | 4.0 | 3.8 | " | 2.5–4.5 |
| Magnesium | 2.1 | 2.0 | mEq/l | 1.7–2.4 |

Table 53 (below) shows changes in the blood electrolytes of Subject No. 9. All values were measured in mEq/l. The first column shows the results before treatment with the plant extract. The second column represents the results by the end of treatment. The third column shows the range of normal values. As the table shows, all the data was within the range of normal values. Moreover, there was an increase in the potassium, sodium, trans-GO, trans-GP, and gamma-GT data. The chlorine data remained the same and the alp data decreased.

TABLE 53

| Electrolytes | Oct 21 1992 | Nov 9 1992 | Normal Values |
|---|---|---|---|
| K | 4.3 | 4.5 | 3.5–5.1 |
| Na | 136 | 141 | 136–146 |
| Cl | 103 | 103 | 98–107 |
| Trans-GO | 19 | 21 | 5–40 |
| Trans-GP | 10 | 18 | 5–40 |
| γ-GT | 16 | 30 | 10–50 |
| Alp | 46 | 37 | 30–125 |

Table 54 (below) shows the results of protein electrophoresis. The first column shows the results prior to treatment with the plant extract. The second column shows the results at the end of the treatment. The third column shows the range of normal values. As shown in table 54, the data is within the range of normal values, except for the a2 and gamma data. Moreover, there were increases in the data for alb, beta, and the alb/glob ratio.

TABLE 54

| Protein Electrophoresis | Oct 21 1992 | Nov 9 1992 | Normal Values |
|---|---|---|---|
| Alb | 55.7 | 58.3 | 52.65 |
| a1 | 3.7 | 3.1 | 2–4.5 |
| a2 | 11.6 | 10.1 | 11–15 |
| β | 9.4 | 9.9 | 6–13 |
| γ | 19.6 | 18.6 | 10–19 |
| Alb/Glob | 1.26 | 1.40 | |

It will now be appreciated that the present invention provides a method for treating HIV positive subjects. The method apparently destroys, neutralizes or at least inhibits the HIV virus. This is evidenced by the fact that the p24 antigen is substantially destroyed or reduced by administering an effective amount of our therapeutically active composition to a subject. The composition used in the method has a medicinal application and results in a negative reading for the p24 (HIV) antigen in a subject that initially tested positive for the p24 (HIV) antigen. Alternatively, the composition used in the method maintains a negative reading for the p24 (HIV) antigen in a subject that initially tested negative for the p24 (HIV) antigen. The composition used in the inventive method includes as an active pharmaceutical an extract of a Mediterranean and West Asiatic plant known as *Asphodelus tenuifolius*.

As the data from the nine HIV positive subjects demonstrates, the administration of the *Asphodelus tenuifolius* plant extract to HIV positive subjects resulted in negative readings for the p24 antigen in those subjects that initially tested positive for the antigen and also maintained negative readings for the p24 antigen in those subjects that initially tested negative for the antigen. Furthermore, the administration of the plant extract to the subjects increased the number of WBC-PMN, lymphocytes, monocytes, platelets, and erythrocytes, especially between 10–20 days of treatment with the plant extract. Moreover, in many instances, the subclasses of T-Cells increased, particularly between 10–20 days of treatment.

In addition to the foregoing, toxicity studies support the conclusion of the plant extracts' non-toxicity.

Therefore, it should be recognized that, while the invention has been described in relation to a preferred embodiment thereof, those skilled in the art may develop a wide variation of structural details without departing from the principles of the invention. Accordingly, the appended claims are to be construed to cover all equivalents falling within the true scope and spirit of the invention.

I claim:

1. A composition for treating an HIV positive subject, having more than 40 picograms/ml of P24 (HIV) antigen comprising a mixture of an aqueous extract of an *Asphodelus tenuifolius* herb, cortisone and a pharmaceutically acceptable carrier.

2. The composition of claim 1 wherein the cortisone is a methylhydrocortisone.

3. A method of treating an HIV positive subject having a P24 (HIV) antigen of more than 40 picograms/ml to lower the P24 (HIV) antigen to not more than 40 picograms/ml which comprises administering to said HIV positive subject, a composition comprising an aqueous extract of at least one plant of *Asphodelus tenuifolius* and a pharmaceutically acceptable carrier.

4. The method of claim 3 wherein said composition also contains a cortisone.

5. The method of claim 4 wherein the cortisone is a methylhydrocortisone.

6. The method of claim 3 wherein said aqueous extract is prepared by adding about 40 to about 60 grams of *Asphodelus tenuifolius* plants to about 1.5 liters to about 2.5 liters of water, boiling the resulting mixture for about 15 to 25 minutes, filtering and recovering said aqueous extract.

7. The method of claim 6 wherein said composition also contains cortisone.

8. The method of claim 7 wherein the cortisone is a methylhydrocortisone.

9. The method of claim 6 wherein said composition also contains cortisone.

10. The method of claim 9 wherein the cortisone is a methylhydrocortisone.

11. A method of treating an HIV positive subject a P24 (HIV) antigen of more than 40 picograms to lower the P24 (HIV) antigen to not more than 40 picograms which comprises administering to said subject, a composition having an aqueous extract of at least one *Asphodelus tenuifolius* plant and a pharmaceutically acceptable carrier.

12. The method of claim 11 wherein said aqueous extract is prepared by adding about 40 to about 60 grams of an *Asphodelus tenuifolius* plant to about 1.5 liters to about 2.5 liters of water, boiling the resulting mixture for about 15 to 25 minutes, filtering and recovering said aqueous extract.

13. The method of claim 11 wherein said composition also contains cortisone.

14. The method of claim 13 wherein said composition also contains cortisone.

* * * * *